United States Patent [19]

Braus et al.

[11] 4,092,292

[45] * May 30, 1978

[54] FLAME RETARDANT COMPOSITIONS

[75] Inventors: Harry Braus, Cincinnati, Ohio; Jay R. Woltermann, Memphis, Tenn.

[73] Assignee: National Distillers and Chemical Corp., New York, N.Y.

[*] Notice: The portion of the term of this patent subsequent to Sep. 7, 1993, has been disclaimed.

[21] Appl. No.: 700,286

[22] Filed: Jun. 28, 1976

Related U.S. Application Data

[63] Continuation-in-part of Ser. No. 505,287, Sep. 12, 1974, Pat. No. 3,979,545.

[51] Int. Cl.$^2$ ............... C08K 3/22; C08K 5/20; C08K 5/16
[52] U.S. Cl. ............... 260/45.75 B; 260/45.85 A; 260/45.85 R; 260/45.9 NC
[58] Field of Search ........... 260/45.85 A, 45.9 NC, 260/553 R, 482 C, 558 R, 561 R, 45.75 B, 45.85 R; 424/300, 320, 322

[56] References Cited

U.S. PATENT DOCUMENTS

| | | | |
|---|---|---|---|
| 2,706,733 | 4/1955 | Reid | 260/553 R |
| 2,724,643 | 11/1955 | Morris et al. | 260/558 R |
| 3,147,219 | 9/1964 | Paterson | 260/561 R |
| 3,160,653 | 12/1964 | Benning et al. | 260/558 R |
| 3,221,044 | 11/1965 | Hoch | 260/558 R |
| 3,288,822 | 11/1966 | Hall et al. | 260/561 R |
| 3,333,970 | 8/1967 | Green | 260/40 |
| 3,752,845 | 8/1973 | Beerman et al. | 260/482 C |
| 3,850,878 | 11/1974 | Murtha et al. | 260/45.85 A |
| 3,865,761 | 2/1975 | Schnabel | 260/45.85 A |
| 3,931,311 | 1/1976 | Thomas | 260/553 R |
| 3,962,246 | 6/1976 | Borer et al. | 260/482 C |
| 3,966,965 | 6/1976 | Sellstedt et al. | 260/561 R |
| 3,969,230 | 7/1976 | Scharf | 260/482 C |
| 3,979,545 | 9/1976 | Braus et al. | 260/45.9 |

Primary Examiner—V.P. Hoke
Attorney, Agent, or Firm—Kenneth D. Tremain

[57] ABSTRACT

The flame resistance of solid polymers are improved by treatment with a halogen containing amide having the formula

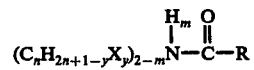

wherein R is lower alkoxy; lower alkoxy carbonyl;

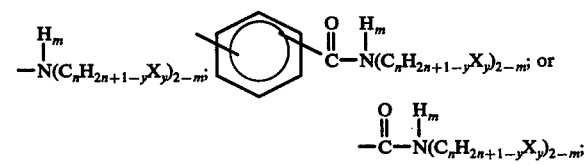

X is chlorine or bromine; m is 0 or 1; n is 1-6; and y is 1-13.

11 Claims, No Drawings

FLAME RETARDANT COMPOSITIONS

CROSS-REFERENCE TO RELATED APPLICATIONS

This application is a continuation-in-part of copending Appln. Ser. No. 505,287 filed Sep. 12, 1974, now U.S. Pat. No. 3,979,545.

BACKGROUND OF THE INVENTION

We have discovered a group of halogenated compounds which can impart an effective degree of flame retardance to solid polymers. In U.S. Pat. No. 3,644,493, there is described 2,3-dihaloalkyl compounds as flame retardant for various natural and synthetic fibers. All of these compounds are esters of allyl alcohol, which are then halogenated in contrast to the present compounds which are derivatives of allyl and diallyl amines and are, in fact, halogenated amides.

Accordingly, it is the object of this invention to provide a new group of compounds for the imparting of flame resistance to solid polymers. This and other objects of the invention will become apparent from the following detailed description of the invention.

SUMMARY OF THE INVENTION

This invention pertains to the imparting of flame resistance to solid polymers by treatment with a halogen containing amide compound.

DESCRIPTION OF THE PREFERRED EMBODIMENTS

The compounds employed in the present invention are halogen containing amides of the formula

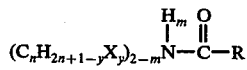

In the foregoing formula, R can be lower alkoxy, i.e., of 1–6 carbon atoms; lower alkoxy carbonyl;

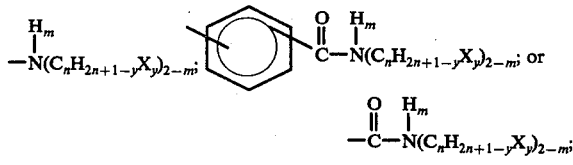

X can be chlorine or bromine; $m$ can be 0 or 1; $n$ can be 1–6; and $y$ can be 1–13.

Illustrative of lower alkoxy groups which can be R in the foregoing formula are methoxy, ethoxy, propoxy, etc. Bis ($\beta,\gamma$-dibromopropyl) ethyl carbamate,

is exemplary of such compounds.

In those compounds where R is lower alkoxy carbonyl, i.e.,

the lower alkyl moiety (A) contains 1–6 carbon atoms. Methoxy carbonyl, ethoxy carbonyl, propoxy carbonyl, etc. are illustrative of such radicals and N,N-bis ($\beta,\gamma$-dibromopropyl) ethyl oxamate,

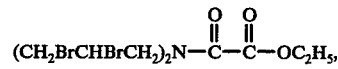

is exemplary of the resulting compounds.

In the compounds in which R is represented by the group

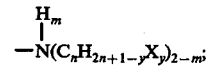

the number of carbon atoms is, as before, 1–6 and the halogen can be chlorine or bromine. N,N-bis ($\beta,\gamma$-dibromopropyl)amino is illustrative of such a radical and tetra($\beta,\gamma$-dibromopropyl)urea,

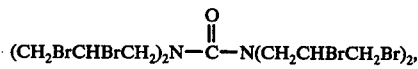

is illustrative of the resulting compound. Where R is represented by the group

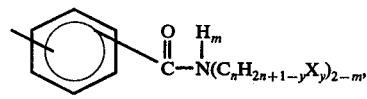

the lower alkyl and halogen groups are as described above and the arylene is phenylene. Illustrative of such a compound is N,N,N',N'-tetrakis ($\beta,\gamma$-dibromopropyl) isophthalamide,

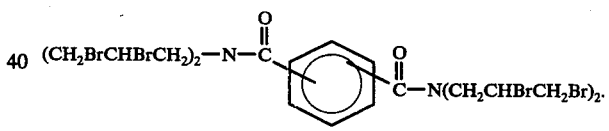

In the compounds in which R is represented by the group

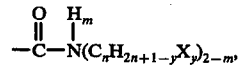

the lower alkyl and halogen are as described above. N-(dibromopropyl) amido is illustrative of such a radical and N,N'-bis($\beta,\gamma$-dibromopropyl) oxamide,

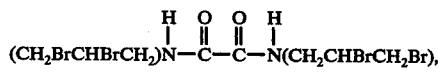

is exemplary of the resulting compound.

The compounds employed in the present invention are known and can be prepared by conventional means.

The foregoing halogen containing amides are conveniently employed in solution form or in the form of an aqueous emulsion, or may be directly admixed with the polymer with agitation at elevated temperature.

The flame retardant compositions may comprise a homogeneous or inhomogeneous intermixture of polymer and agent, the latter being incorporated intimately in a compounding operation, applied to the surface as a coating, or absorbed into a porous e.g. foamed article. Preferably, molded articles comprise an intimate admixture of flame retardant agent and polymer, to a level of 10–20 percent by weight of flame retardant. Obviously, lesser or greater proportions may be empolyed within economic and effectiveness limits, having regard for the form of the finished articles as flakes, pellets, film and the like. Typically, a flame retardant amount, for example 2 to 5 weight percent up to 10–15 percent or more of the flame retardant will be introduced to the polymer.

In the case of solution or dispersion application, the amides can vary in concentration over a wide range of from about 5–25 weight percent and preferably about 10–20 weight percent and are applied to the same add-on level, preferably 10–15 weight percent.

Suitable solvents for the halogen containing amides include the halogenated hydrocarbons such as trichloroethylene, perchloroethylene, methylene, chloride, and the like; ether, and any other organic solvents in which the halogen containing amides are soluble.

Suitable emulsifying agents for maintaining the amides in aqueous emulsions include anionic, cationic and non-ionic dispersing agents or surfactants. Suitable nonionic surfactants include the alkyl phenoxy poly(ethyleneoxy) ethanols, and the dialkyl phenoxy poly(ethyleneoxy) ethanols, preferably those wherein the alkyl substituents have 5–12 carbon atoms and which have 1–20 ethyleneoxy groups. Typical members are cotyl phenoxy poly(ethyleneoxy)ethanol, nonyl phenoxy poly(ethyleneoxy)ethanol dodecylphenoxy poly(ethyleneoxy) ethanol. Also useful are the fatty acid esters of polyhydric alcohols or ether alcohols such as glycerol monostearate; esters of ethylene glycol, diethylene glycol, triethylene glycol and polyethylene glycol such as the condensation product of oleic acid with ethylene oxide; and fatty esters of sugar alcohols. Suitable anionic surfactants include the alkali metal alkyl benzene sulfonates such as sodium and potassium dodecyl benzene sulfonate; the alkali metal alkyl sulfates such as sodium lauryl sulfate; the sulfonated aliphatic polyesters, free acids of complex phosphate esters, sodium salts of complex phosphate esters, sodium salts of disproportionated wood resin. Suitable cationic surfactants include the fatty amides of monoethanol amines, fatty nitriles and fatty acid amides such as olein morpholide. Also useful as cationic agents are the polyoxy ethylated alkyl amines.

The solid polymers which can be treated in accordance with the present invention include the polyamides such as 6-, and 6,6-nylons, polyesters, polyolefins such as polypropylene or polyethylene, polyurethanes, acrylics, cellulose triacetates such as Arnel, and copolymers and blends thereof.

The fire retardant compounds of the instant invention can be supplied to the polymer compositions in conventional manner. A suitable method involves incorporation by means of a high shear internal mixer such as a Banbury, or any continuous mixers, mixing extruders, and two-roll mills.

In the case of solvent application, the polymer article is immersed in the solution or emulsion for a period of from about ¼ to 2 hours, preferably about one-half and the compound is deposited therefrom and the solvent removed by evaporation or vaporization.

The incorporation of flame retardant may be carried out at temperatures varying over a wide range of from about 30°–100° C.; in the case of direct intermixture, the temperature is preferably elevated, and ranges from about 90°–100° C., whereas with solvent application ambient temperature may be employed. Wherever desirable a conventional stabilizer e.g., one or more antioxidants may be employed, or about 5–20% of an antimony compound such as $Sb_2O_3$ used in conjunction with the halogen containing compound to achieve a higher degree of flame resistance in these solid thermoplastic polymers.

The following Examples are set forth in order to further illustrate the present invention. Throughout this specification and claims, all temperatures are in degrees centigrade and all parts and percentages are by weight unless otherwise specified.

EXAMPLE I

Bis($\beta,\gamma$-dibromopropyl)ethylcarbamate was prepared by the bromination of N,N-(diallyl)ethylcarbamate as follows:

Charged into a one liter, a 3-necked flask equipped with the necessary adjuncts were diallylamine, 48.6 g (0.5 mole), triethylamine, 50.6 g (0.5 mole) and 200 ml of ether. This was cooled to 0° C. and ethylchloroformate, 54.3 g (0.5 mole) was added slowly dropwise with constant stirring. The addition took 3½ hours, maintaining a temperature of 0° C. An additional 350 ml of ether was added to maintain fluidity. After warming to room temperature, the solid amine salt was filtered and the ether distilled from the filtrate. The resulting product was purified by distillation under reduced pressure. B.P. 40.5°– 41° C. at 0.1 mm Hg. — Yield 71%.

Charged into a one liter, 3-necked flash equipped with a stirrer, $N_2$ inlet, thermometer, dropping funnel and condenser were N,N-diallylethylcarbamate, 57.8 g (0.342 mole), and 300 ml of chloroform. This was cooled to 0° C. and with vigorous stirring, bromine, 109.3 g (0.684 mole) was added dropwise. When the addition was complete, the bath was warmed to room temperature and allowed to stand overnight. The chloroform was then distilled and finished at 0.5 mm pressure. Yield 81.2%.

A sample was submitted for mass spectra which showed a compound of mass 485 containing 4 bromines. This confirms the structure of the compound.

Bis($\beta,\gamma$-dibromopropyl)ethylcarbamate (40 g) is dispersed in ethylene glycol (80 g) using as emulsifier, Duponal OS (2 g), an amine long chain alcohol sulfate. The mixture is heated with stirring until a homogeneous dispersion is obtained. The solution is then cooled to room temperature. Before use, this dispersion is emulsified with water (150 g) preferably using a colloid mill.

EXAMPLE 2

N,N-bis($\beta,\gamma$-dibromopropyl)ethyloxamate was prepared by the bromination of N,N-diallylethyl oxamate as follows:

Ethyloxalate, 146.1 g (1.0 mole), was charged into a 3-necked flask equipped with a mechanical stirrer, dropping funnel, condenser and drying tube. Diallylamine, 97.2 g (1.0 mole) was slowly added with constant stirring. There was a moderate exotherm during the addition until approximately one-half the amine was added, at which time the temperature declined. When the addition was complete, the bath was heated to 80°–90° C. for 4 hours and then cooled by standing overnight.

The product was then fractionated and vacuum distilled and the portion boiling at 105°–106° C. at 1 mm Hg was collected. The product was submitted for mass spectra determination which showed a mass of 197 and then expected fragments of the desired product, N,N-diallylethyloxamate.

The N,N-diallylethyloxamate, 77.3 g (0.39 mole), dissolved in 100 ml of chloroform, was charged to a one liter, 3-necked flask equipped with a stirrer, thermometer, dropping funnel condenser and drying tube. The solution was cooled to 4° C. and bromine, 124.7 g (0.78 mole), was slowly added. When all the bromine was added, the chloroform was distilled at atmospheric pressure. The remaining chloroform was removed under reduced pressure (water pump). The residue was taken up in benzene, filtered and evaporated under a stream of $N_2$. M.P. 160° C. (with decomposition). Mass spectra analysis confirmed the desired compound.

N,N-bis($\beta,\gamma$-dibromopropyl)ethyloxamate (30 g) is dissolved in perchloroethylene (180 ml) using Triton X-100 (5 g) which is an octylphenoxypolyethoxy ethanol.

EXAMPLE 3

Tetra($\beta,\gamma$-dibromopropyl)urea was prepared by the bromination of bis(diallyl)urea as follows:

Charged under dry $N_2$ to a one liter, 3-necked flask equipped as in the previous preparation, were diallylamine, 44.3 g (0.456 mole) and triethylamine, 46.1 g (0.456 mole), in 100 ml of dry benzene. This was cooled with stirring to 0° C. and to this was carefully added phosgene in benzene, 237.8 g (0.228 mole). The pot temperature was maintained at 0°-5° C. by the regulation of addition rate. When the addition was complete, the amine hydrochloride was filtered off, the benzene washed with $H_2O$ and dried. The benzene was then removed under reduced pressure. Yield — 41.3 g 82%–83% theory. Mass spectra confirmed the expected structure.

Bromination of bis(diallyl) urea was effected as follows: charged into a dry one liter, 3-necked flask with the usual equipment were bis(diallyl)urea, 39.4 g (0.18 mole), and 100 ml chloroform. This was cooled to 0° C. with constant stirring. Then, 115.1 g (0.72 mole) bromine in 50 ml of chloroform was slowly added, maintaining a temperature of 0°-5° C. Additional amounts of chloroform (total 150 ml) were added to keep the reaction mixture fluid. When the addition was complete, the batch was stirred for ½ hour until it reached room temperature. The solvent was distilled. The residue consisted of a thick syrup which set up to an amorphous solid.

Tetra($\beta,\gamma$-dibromopropyl)urea (25 g) was dissolved in 100 ml of perchloroethylene using as emulsifying agent, Triton X-100.

EXAMPLE 4

N,N,N',N'-tetrakis($\beta,\gamma$-dibromopropyl) isophthalamide was prepared by the bromination of tetraallylisophthalamide. This latter compound was prepared as follows:

Charged, under dry $N_2$ to a one liter, 3-necked flask equipped with a stirrer, $N_2$ inlet, thermometer, dropping funnel and condenser, were diallylamine, 88.6 g (0.912 mole), and triethylamine, 92.3 g (0.912 mole), in 300 ml of ether. Isophthaloylchloride, 92.5 g (0.456 mole), dissolved in 200 ml of ether, was slowly added maintaining a temperature of approximately 0°-5° C. Addition was complete in 3½ hours. Evaporation of the ether yielded 129.6 g of product — 87.5% of theory.

Bromination of the bis amide was accomplished as follows: charged under dry nitrogen to a one liter, 3-necked flask equipped with a stirrer, $N_2$ inlet, dropping funnel and condenser was tetraallylisophthalamide, 123.8 g (0.38 mole) and 200 ml of chloroform. This was cooled with stirring to 0° C. and there was slowly added bromine, 243.0 g (1.52 mole), diluted with chloroform. The temperature was kept at −5° to 5° C. The product began to separate out and more solvent was added. When the addition was completed, the batch was stirred at room temperature for 1 hour. The mixture was then heated to remove solvent. There remained a thick syrup which set up to an amorphous fluid.

N,N,N',N'-tetrakis($\beta,\gamma$-dibromopropyl) isophthalamide (30 g) is emulsified in water using IGEPAL CA-420 (5 g) an octylphenoxypoly(ethyleneoxy)ethanol. Emulsification is hastened by use of heat and ultrasonic vibration.

EXAMPLE 5

N,N'-bis($\beta,\gamma$-dibromopropyl)oxamide was prepared by the bromination of N,N'-bis(allyl) oxamine. The latter compound was prepared as follows:

Charged to a 2-liter, 3-necked flask were allylamine, 114.2 g (2.0 mole) and 150 ml of ethanol. To this solution, ethyl oxalate, 146 g (1.0 mole) in 50 ml of ethanol was slowly added with stirring. The reaction was exothermic and when the temperature reached 40° C., cooling was applied to 20°-30° C. at which temperature the remaining ethanol was added. The mixture was cooled to room temperature and allowed to stand overnight. The batch was further cooled in ice and filtered and the filter cake washed with ethanol and air dried. Yield — 123.7 g, M.P. 156.5°-157.5° C.

The bromination was carried out in the usual manner using glacial acetic acid as the solvent. The yield was 102.1 g (83.5% of theory), M.P. 222°-224° C. Mass spectra confirmed the structure in both molecular weight and bromine content.

N,N'-bis($\beta,\gamma$-dibromopropyl)oxamide (30 g) is dissolved in 110 ml of perchloroethylene using IGEPAL CA-420 (5 g).

EXAMPLE 6

A series of flame retardant agents in accordance with the invention was formulated in a Banbury mixer at 300°-320° F. with polypropylene copolymer (comprising a minor proportion of copolymerized ethylene (Pro-Fax 1823 Hercules, M.I. 0.4, dens. 0.901-0.902) at a 10 percent level by weight thereof, molded into test plaques, and performance evaluated with results as follows:

|  | Control | Flame Retardant Agents | | | |
|---|---|---|---|---|---|
|  |  | 1 | 2 | 3 | 4 |
| Oxygen Index |  | 25.3 | 25.0 | 25.0 | 24.9 |
| Avg. 1st burn, sec. | Burns to Consumption | 0 | 0 | 0 | 0 |
| Avg. 2d burn, sec. |  | 0 | 0 | 0 | 0 |
| Avg. afterglow, sec. |  | 38.0 | 40.4 | 55.8 | 45.6 |
| Flame retardant agents |  |  |  |  |  |
| 1. N,N'-bis ($\beta,\gamma$-dibromopropyl) ethyl oxamate |
| 2. bis(tetrabromo dipropyl) isophthalamide |
| 3. tetra($\beta,\gamma$-dibromo propyl) urea |
| 4. N,N'-bis($\beta,\gamma$-dibromopropyl) oxamide |

Notes:

All materials were formulated identically, with 5 percent antimony oxide (based on polymer) and a stabilizer system comprising 0.5 percent mark 645 (a proprietary, tin stabilizer available from Argus Chemical Corp.), 0.3 percent Irganox 1010 (tetrakis[3-(3,5-di-t-butyl-4-hydroxyphenyl propionoxymethyl] methane from Ciba Geigy), and 0.3 percent dilaurylthiodipropionate.

The control burned to consumption upon application of flame, whereas all of the flame retarded materials were self-extinguishing on first and second application of flame, and exhibited a relatively short afterglow. There was no drip of the flame retarded materials, as distinct from the control.

Various changes and modification can be made in the process and products of this invention without departing from the spirit and the scope thereof. The various embodiments set forth herein were for the purpose of further illustrating the invention but were not intended to limit it.

We claim:

1. A flame retarded composition comprising a solid polymer and a flame retardant amount of a halogen containing amide having the formula:

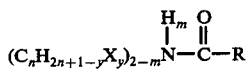

wherein R is lower alkoxy; lower alkoxy carbonyl;

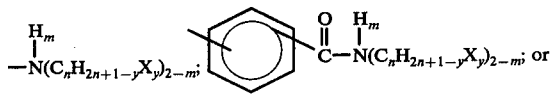

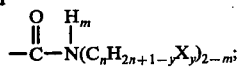

X is chlorine or bromine; $m$ is 0 or 1; $n$ is 1–6; and $y$ is 1–13.

2. The amide of claim 1 wherein the lower alkoxy radical contains 1–6 carbon atoms and the lower alkoxy carbonyl radical contains 2–7 carbon atoms.

3. The composition of claim 1, wherein said polymer is a polyolefin.

4. The composition of claim 3, wherein said halogen containing amide is N,N'-bis($\beta$,$\gamma$-dibromopropyl) oxamide.

5. A flame retarded polymeric composition comprising a homogeneous admixture of polypropylene and a flame retardant amount up to about 20 percent by weight of the polymer of a halogen contaning amide selected from the group consisting of N,N'-bis($\beta$,$\gamma$-dibromopropyl)ethyl oxamate, N,N,N',N'-tetrakis($\beta$,$\gamma$-dibromopropyl) isophthalamide, tetra ($\beta$,$\gamma$-dibromopropyl) urea, and N,N'-bis($\beta$,$\gamma$-dibromopropyl) oxamide.

6. The composition of claim 5, wherein said composition also comprises from about 5 to about 20 percent by weight of polymer, of antimony oxide.

7. The composition of claim 6, comprising about 10 percent by weight of polymer of N,N'-bis($\beta$,$\gamma$-dibromo propyl) oxamide.

8. A molded article composed of the composition of claim 7.

9. The composition of claim 1 wherein the amount of amide is, by weight, about 5 to 25%.

10. The composition of claim 1, wherein said composition also comprises about 5 to about 20% by weight of polymer, of antimony oxide.

11. The composition of claim 1 wherein the polymer is selected from the group consisting of polyamides, polyesters, polypropylene, polyethylene, polyurethane, acrylics, cellulose triacetate, copolymers thereof and blends thereof.

* * * * *